(12) United States Patent
Drenser et al.

(10) Patent No.: US 11,041,863 B2
(45) Date of Patent: Jun. 22, 2021

(54) FRIZZLED-4 MUTATION INDICATOR OF RETINOPATHY AND INTRAUTERINE GROWTH RESTRICTION

(71) Applicant: RETINAL SOLUTIONS LLC, Ann Arbor, MI (US)

(72) Inventors: Kimberly Drenser, Novi, MI (US); Michael T. Trese, Novi, MI (US); Antonio Capone, Novi, MI (US)

(73) Assignee: RETINAL SOLUTIONS LLC, Ann Arbor, MI (US)

( * ) Notice: Subject to any disclaimer, the term of this patent is extended or adjusted under 35 U.S.C. 154(b) by 325 days.

(21) Appl. No.: 15/656,558

(22) Filed: Jul. 21, 2017

(65) Prior Publication Data
US 2018/0024138 A1    Jan. 25, 2018

Related U.S. Application Data

(60) Provisional application No. 62/365,123, filed on Jul. 21, 2016.

(51) Int. Cl.
| | | |
|---|---|---|
| *G01N 33/483* | (2006.01) | |
| *G01N 33/49* | (2006.01) | |
| *A61K 38/00* | (2006.01) | |
| *G01N 33/68* | (2006.01) | |
| *A61K 38/17* | (2006.01) | |

(52) U.S. Cl.
CPC ....... *G01N 33/689* (2013.01); *A61K 38/1709* (2013.01); *G01N 2800/368* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 5,270,163 A | 12/1993 | Gold et al. | |
| 5,475,096 A | 12/1995 | Gold et al. | |
| 5,567,588 A | 10/1996 | Gold et al. | |
| 5,595,877 A | 1/1997 | Gold et al. | |
| 5,637,459 A | 6/1997 | Burke et al. | |
| 5,660,985 A | 8/1997 | Pieken et al. | |
| 5,670,637 A | 9/1997 | Gold et al. | |
| 5,683,867 A | 11/1997 | Biesecker et al. | |
| 5,696,249 A | 12/1997 | Gold et al. | |
| 5,707,796 A | 1/1998 | Gold et al. | |
| 6,011,020 A | 1/2000 | Gold et al. | |

(Continued)

OTHER PUBLICATIONS

Dailey et al., Fad4 gene mutations in familial exudative vitreoretinaopathology and retinaopathyof rematurity in patients, Invest. Ophth. Vis. Sci., 49:3111, May 2008.*

(Continued)

*Primary Examiner* — Claire Kaufman
(74) *Attorney, Agent, or Firm* — Blue Filament Law PLLC (57) ABSTRACT

A method for determining the necessity of a pre-term birth treatment is provided based on obtaining a biological sample from a subject. The biological sample is analyzed for the presence of (P33S;P168S) Frizzled4 (Fzd4) gene variation. The subject or a fetus thereof is then treated for a proclivity to pre-term birth. The Fzd4 protein itself can also be analyzed for the (P33S;P168S) Fzd4 mutation.

7 Claims, 4 Drawing Sheets

(56) References Cited

U.S. PATENT DOCUMENTS

2012/0282230 A1* 11/2012 Drenser ............. A61K 38/1774
424/93.21

OTHER PUBLICATIONS

Lo, YMD, Molecular testing of urine:catching DAN on the way out, Clin. Chem. 46(8): 1039-1040, 2000.*

Dresner et al., Clinical presentation and genetic correlation of patients with mutations affectin gthe FZD4 gene, Arch. Ophth. 127(12):1649-1654, 2009.*

Anderson et al., Determinants of size at birth in a Candian population, Am. J. Obst. Gyn. 150(3):236-244, Oct. 1, 1984, Abtract only.*

Mutlu et al., Treatment of retinopathy of prematurity:a review of conventional and promising new therapeutic options, Int. J. Ophth, 6 (2):228-236, 2013.*

Usha et al., Placental insufficiency and fetal growth restriction, J. Obst. Gynecol. India, 6(5):505-511, Oct. 2011.*

Takunaga et al., Retinal vascular rescue of oxgen-induced retinopathy in mice by norrin, Invest. Opthalmol. Vis. Sci. 54:222-229, 2013.*

Qin et al., Complexity of the genotype-phenotype correlation in familial exudative vitreoretinopathy with mutations in the LRP5 and/or FZD4 genes, Hum. Mutat. 26(2), 104-112, 2005.*

Koullali et al., Risk assessment and management to prevent preterm birth,.Sem. Fetal Neonat. Med. 21:80-88, 2016.*

Dailey et al., Frizzled-4 variaions associaed with retinopahty and intrauterine growth retardation, Ophthalmol.122:1917-1923, 2, available online Jun. 25, 2015.*

Connolly, S.E. et al., "Characterization of Vascular Development in the Mouse Retina", Microvascular Research, Dec. 1988, pp. 275-290, vol. 36, Issue 3, Copyright Academic Press, Inc. (1988).

Willert, Karl and Nusse, Roel, "β-catenin: a key mediator of Wnt signaling", Current Opinion in Genetics & Development, Feb. 1998, pp. 95-102, vol. 8, Issue 1, Copyright Current Biology Ltd (1998).

Kramer, M.S. et al., "A New and Improved Population-Based Canadian Reference for Birth Weight for Gestational Age", Pediatrics, Aug. 2001, pp. 1-9, vol. 108, Issue 2: E35, Copyright American Academy of Pediatrics (2001).

Provis, Jan M., "Development of the Primate Retinal Vasculature", Progress in Retinal and Eye Research, Nov. 2001, pp. 799-821, vol. 20, Issue 6, Copyright Elsevier Science Ltd. (2001).

Fruttiger, Marcus, "Development of the Mouse Retinal Vasculature: Angiogenesis Versus Vasculogenesis", Investigative Ophthalmology & Visual Science, Feb. 2002, pp. 522-527, vol. 43, Issue 2, Copyright Association for Research in Vision and Ophthalmology (2002).

Robitaille, J. et al., "Mutant frizzled-4 disrupts retinal angiogenesis in familial exudative vitreoretinopathy", Nature Genetics, Sep. 2002 (Published Online: Aug. 12, 2002), pp. 326-330, vol. 32, Issue 2, Copyright Nature Publishing Group (2002).

Kondo, H. et al., "Frizzled 4 gene (FZD4) mutations in patients with familial exudative vitreoretinopathy with variable expressivity", British Journal of Ophthalmology, Oct. 2003, pp. 1291-1295, vol. 87, Issue 10, Copyright British Journal of Ophthalmology (2003).

Toomes, C. et al., "Mutations in LRP5 or FZD4 Underlie the Common Familial Exudative Vitreoretinopathy Locus on Chromosome 11q", American Journal of Human Genetics, Apr. 2004 (Published Online Mar. 11, 2004), pp. 121-730, vol. 74, Issue 4, Copyright the American Society of Human Genetics (2004).

Ohlmann, A. et al., "Ectopic Norrin Induces Growth of Ocular Capillaries and Restores Normal Retinal Angiogenesis in Norrie Disease Mutant Mice", The Journal of Neuroscience, Feb. 16, 2005, pp. 1701-1710, vol. 25, Issue 7, Copyright Society for Neuroscience (2005).

Macdonald, M.L. et al., "Genetic variants of frizzled-4 gene in familial exudative vitreoretinopathy and advanced retinopathy of prematurity", Clinical Genetics, Apr. 2005, pp. 363-366, vol. 67, Issue 4, Copyright Blackwell Munksgaard (2005).

Hsieh, M. et al., "Mice Null for Frizzled4 (Fzd4-/−) are Infertile and Exhibit Impaired Corpora Lutea Formation and Function", Biology of Reproduction, Dec. 2005 (Published Online: Aug. 10, 2005), pp. 1135-1146, vol. 73, Issue 6, Copyright the Society for the Study of Reproduction, Inc. (2005).

Inoue, T. et al., "Activation of Canonical Wnt Pathway Promotes Proliferation of Retinal Stem Cells Derived from Adult Mouse Ciliary Margin", Stem Cells, Jan. 2006 (Published Online: Oct. 13, 2005), pp. 95-104, vol. 24, Issue 1, Copyright AlphaMed Press (2005).

Bizzaro, M.J. et al., "Genetic Susceptibility to Retinopathy of Prematurity", Pediatrics, Nov. 2006, pp. 1858-1863, vol. 118, Issue 5, Copyright the American Academy of Pediatrics (2006).

Planutis, K. et al., "Regulation of norrin receptor frizzled-4 by Wnt2 in colon-derived cells", BMC Cell Biology, Mar. 26, 2007, pp. 1-10, vol. 8, Issue 12, Copyright Planutis et al. (2007).

Qin, M. et al., "Moderate reduction of Norrin signaling activity associated with the causative missense mutations identified in patients with familial exudative vitreoretinopathy", Human Genetics, Jan. 2008 (Published Online: Oct. 23, 2007), pp. 615-623, vol. 122, Issue 6, Copyright Springer-Verlag (2007).

Ells, A. et al., "Severe retinopathy of prematurity associated with FZD4 mutations", Ophthalmic Genetics, Mar. 2010, pp. 37-43, vol. 31, Issue 1, Copyright Informa Healthcare USA, Inc. (2010).

Sonderegger, S., Pollheimer, J., Knöfler, M. "Wnt Signalling in Implantation, Decidualisation and Placental Differentiation—Review", Placenta, Oct. 2010 (Published Online: Aug. 15, 2010), pp. 839-847, vol. 31, Issue 10, Copyright Elsevier Ltd. (2010).

Kaloglu, C., Cesur, I., Bulut, H.E., "Norrin immunolocalization and its possible functions in rat endometrium during the estrus cycle and early pregnancy", Development, Growth & Differentiation, Sep. 2011, pp. 887-896, vol. 53, Issue 7, Copyright the Authors & Japanese Society of Developmental Biologists (2011).

Toomes, C. and Downey, L., "Familial Exudative Vitreoretinopathy, Autosomal Dominant", Mar. 21, 2005 (Last Revision: Sep. 22, 2011); In: Pagon, R.A., Adam, M.P., Ardinger, H.H. et al., Editors; GeneReviews® [Internet]; Seattle (WA): University of Washington, Seattle; 1993-2017. Available from: https://www.ncbi.nlm.nih.gov/books/NBK1147/.

Macdonald, L.J. et al., "Prokineticin 1 induces Dickkopf 1 expression and regulates cell proliferation and decidualization in the human endometrium", Molecular Human Reproduction, Oct. 2011 (Published Online: May 5, 2011), pp. 626-636, vol. 17, Issue 10, Copyright the Authors (2011); Published by Oxford University Press on behalf of the European Society of Human Reproduction and Embryology.

Matsuura, K. et al., "Identification of a link between Wnt/β-catenin signalling and the cell fusion pathway", Nature Communications, Nov. 22, 2011, pp. 1-9, vol. 2, Issue 548, Copyright Macmillan Publishers Limited (2011).

Van Der Horst, P.H. et al., "Interaction between sex hormones and WNT/β-catenin signal transduction in endometrial physiology and disease", Molecular and Cellular Endocrinology, Jul. 25, 2012 (Published Online: Jun. 22, 2011), pp. 176-184, vol. 358, Issue 2, Copyright Elsevier Ireland Ltd. (2011).

1000 Genomes Project Consortium; Abecasis, G.R. et al., "An integrated map of genetic variation from 1,092 human genomes", Nature, Nov. 1 2012 (Author Manuscript Available in PMC: May 1, 2013), pp. 56-65, vol. 491, Issue 7422.

Milhem, R.M. et al., "Identification of the Cellular Mechanisms That Modulate Trafficking of Frizzled Family Receptor 4 (FZD4) Missense Mutants Associated With Familial Exudative Vitreoretinopathy", Biochemistry and Molecular Biology, Jun. 2014, pp. 3423-3431, vol. 55, Issue 6, Copyright the Association for Research in Vision and Ophthalmology, Inc. (2014).

* cited by examiner

FRIZZLED-4 MUTATION INDICATOR OF RETINOPATHY AND INTRAUTERINE GROWTH RESTRICTION

CROSS-REFERENCE TO RELATED APPLICATION

This application claims priority of U.S. Provisional Patent Application Ser. No. 62/365,123 filed Jul. 21, 2016, which is incorporated herein by reference.

FIELD OF THE INVENTION

The present invention is directed generally to methods for predicting premature births; and in particular, to using the association between mutations affecting the Wnt-signaling receptor (Fzd4), inherited vitreoretinopathies and Retinopathy of Prematurity as an indicator of pre-term births and whether a pregnant subject merits clinical treatment to mitigation pre-term birth.

BACKGROUND OF THE INVENTION

Preterm birth is a common cause of neonatal morbidity and mortality. An extensive body of evidence indicates that infection is associated with preterm delivery and with low birth weight of the infant. This results in a series of treatments involving antibiotics that can themselves be harmful. Additionally, this conventional wisdom does not account for an appreciable number of pre-term births when infection is not present. As any treatment during pregnancy that is not needed is a concern, while pre-term birth leads to complex neonatal treatments regimes that sometime leave the child with permanent deficiencies. While screening for infections such as bacterial vaginosis and other pathogens is straightforward, these screening fail to detect genetic predispositions to pre-term birth.

Proper vascular modeling in the retina is essential for ocular development and visual acuity. Abnormal vessel growth during development or in adulthood produces several diseases such as retinopathy of prematurity, diabetic retinopathy, and age-related macular degeneration. Normal retinal development occurs through vessels forming at the optic nerve head and spreading over the retina to form a dense network (Connolly, S E, et al., Microvasc Res, 1988; 36:275-290; Provis, J M, Prog Retin Eye Res, 2001; 20:799-821; Fruttiger, M, Invest Ophthalmol Vis Sci, 2002; 43:522-527). Development proceeds through formation of primary vessels along the surface of the developing retina from which divergent vessels begin to extend into the capillary beds that form the outer and inner plexiform layers of the retina (Connelly, 1988; Provis, 2001, Fruttiger, 2002). Vascular development is mediated by a series of growth factors that direct formation and extension of new vessels. Retinal development is unique in the concentration and types of signaling mediators employed to promote angiogenic sprouting from the primary vascular network and the formation of the final capillary architecture (Ohlmann, A, et al., J Neurosci, 2005; 25:1701-1710).

One factor involved in formation of primary retinal vascular and retinal capillaries is the transmembrane receptor frizzled-4 (Fzd4). Mutations in the gene encoding the Fzd4 receptor are observed in patients diagnosed with autosomal dominant Familial Exudative Retinopathy (AdFEVR), (Toomes C, Downey L, GeneReviews, NCBI, 2008, and retinopathy of prematurity (ROP). MacDonald, M L, Clin Genet., 2005; 67:363-6). In both diseases, the patient is born with enlarged and tortuous retinal vessels and an area of avascular peripheral retina. Additionally, varying degrees of subretinal exudation, vitreoretinal traction, and abnormal extraretinal vessels/neovascularization may occur.

Fzd4 is a 537 amino acid, seven transmembrane receptor that functions via three signaling pathways. Proper Fzd4 ligand binding and signal transduction are required for normal retinal vascular development. Several ligands are known to interact with Fzd4 to produce signaling events. These include the Wnt ligands (Wnt-3a, Wnt-8, and Wnt-5a) and the non-Wnt ligand Norrin.

Fzd4 signaling is mediated by three independent signal transduction pathways each of which is believed to be activated by binding of any of the Fzd4 ligands. These pathways include the canonical Wnt/β-Catenin pathway, the planar cell polarity pathway, and the Wnt-$Ca^{2+}$ pathway. Signaling is initiated by ligand binding to Fzd4 alone or along with its co-receptor LRP5.

The most recognized and studied Fzd4 signaling mechanism is the Wnt/β-Catenin pathway. Ligand binding inactivates glycogen synthase kinase (GSK) 3β and Axin resulting in dephosphorylation of -catenin and its translocation to the nucleus. The inactivation of these proteins stabilizes β-Catenin, which subsequently accumulates in the cell nucleus and activates the transcription factor and lymphoid enhancer-binding factor (TCF/LEF-1) family of DNA binding proteins regulating transduction of target genes crucial in the G1-S-phase transition, encoding proteins such as cyclin D1, VEGF, or c-Myc (Willert K, and Nusse R, Curr Opin Genet Dev, 1998; 8:95-102). These pathways promote stimulation and proliferation of retinal stem cells (Inoue, T, et al., Stem Cells, 2006; 24:95-104).

The planar cell polarity pathway is activated by any ligand binding to Fzd4. Unlike the canonical pathway, the planar cell polarity pathway does not require association of Fzd4 with LRP5 possibly promoting differential regulation and expression of this pathway based on the presence or activity of LRP5. This pathway is propagated by activation of disheveled protein (Dsh) which leads to activation of Rho or Rac promoting expression of alternative signal transduction pathways. The planar cell polarity pathway mediates cytoskeletal organization and cell migration.

Wnt-signaling is a ubiquitous pathway that modulates cellular and tissue differentiation. In regards to eye development, a particular Wnt-pathway, Norrin-Fzd4, has been identified as playing a role in retinal angiogenesis. Signaling through this pathway is necessary for development and maintenance of retinal vasculature. Mutations affecting genes of this pathway may result in several pediatric vitreoretinopathies, such as Norrie Disease, Familial Exudative Vitreoretinopathy (FEVR), and Pseudoglioma and Osteoporosis Syndrome. Additionally, Retinopathy of Prematurity (ROP) has been associated with mutations in this pathway, and Wnt-pathway mutations have been reported in Coats Disease and Persistent Fetal Vasculature (PFV).

A common characteristic of these Wnt-associated vitreoretinopathies is dysgenesis of retinal vessels with variable breakdown of the blood-retina barrier, often leading to exudative and tractional retinal detachments. Norrie Disease is an X-linked disorder and has the most severe phenotype resulting in blindness, often present at birth. It is often caused by mutations in the conserved cysteine residues of the NDP gene which comprise the necessary tertiary structure involved in ligand-receptor binding. In PFV, the premature vasculature of the eye does not regress appropriately resulting in the formation of a fibrous stalk that extends from the optic disk to the posterior lens capsule. Since the fibrous stalks are common in both PFV and ND the two disorders are often indistinguishable if bilateral disease is present. FEVR occurs in an X-linked (NDP), autosomal recessive (LRP5) or autosomal dominate inheritance pattern (Fzd4, TSpan12, ZNF408). Most reported cases of AdFEVR have been associated with heterozygous mutations in the Fzd4 gene.

ROP and FEVR have overlapping phenotypes and an ambiguous birth history may confuse the diagnosis. Generally, ROP is distinguished from FEVR by premature birth and the lack of a family history. A combination of incomplete peripheral retinal vessel development and exposure to a relatively high oxygen environment (compared to in utero) is believed to set the stage for development of ROP. However, gestational age, birth weight, and systemic health alone do not predict the progression to retinopathy, thus requiring that all at-risk infants have routine screening exams every 1-2 weeks. The overlap in retinal characteristics has supported the hypothesis that a predisposition for ROP is created by genetic alterations. In fact, a twin study demonstrated that there is a likely genetic predisposition for ROP development in 80% of premature infants with retinopathy. Mutations in both the NDP and Fzd4 genes have been reported in ROP cases and make Wnt-pathway mutations a likely candidate as a risk factor for developing ROP.

A link between premature birth and ROP may lie with altered Wnt signaling. Studies have shown that Norrin-Fzd4 signaling affects angiogenesis in the female reproductive system. Markers for angiogenesis and vascular formation are reduced in the corporo lutea of Fzd4 null mice and these mice are infertile. Also, Fzd4 mRNA localizes to vessels and stroma surrounding the mouse embryo. Similarly, norrin has been localized to the uterine blood vessels and decidual cells of rats, and NDP knockout mice have defects in vascular development and decidualization in pregnancy that leads to embryonic loss. In humans, the expression of NDP has been established in the placenta and Fzd4 expression has been localized to placental villous mesenchymal cells.

Infants expressing the (P33S;P168S) Fzd4 variant have significantly reduced weight for gestational age (GA). The lower than normal birth weights for GA present in the ROP patients with the (P33S;P168S) variant compared to the other premature infants supports the theory that the Fzd4 receptor is involved in placental formation and/or fetal growth. In fact, 5 of 7 ROP patients with the variation, were in the group that had the highest birth weight deficits and were defined as small for gestational age. Presumably, the presence and/or absence of the sequence variation in the mothers would also be a complicating factor in fertility and/or placental development as would additional mutations in NDP; Fzd4 pathway genes.

Abnormalities in the Fzd4 and LRP5 receptors result in the phenotypically similar conditions FEVR, ROP, and possibly Norrie disease (Robitaille, J, et al., Nature Genet, 2002; 32:326-330; Kondo, H, et al., Br J Opthalmol, 2003; 87:1291-1295; Toomes, C, et al., Am J Hum Genet. 2004; 74:721-730). The close association between the phenotypes produced by Norrin mutations and mutations in the Fzd4 and LRP5 receptors bolsters the hypothesis that these molecules form a functional signaling group (Planutis, K, et al., BMC Cell Biology, 2007; 8:12).

Based on a large collected database of DNA from patients with disorders including FEVR, ROP, and Norrie disease, a routine analysis of the Norrie Disease Protein (NDP), frizzled-4 (Fzd4), and tetraspanin 12 (TSpan12) gene sequences using Sanger sequencing has provided an indication of a high incidence of one particular Fzd4 gene sequence variation (P33S;P168S) in ROP. Furthermore, when looking specifically at the incidence of this Fzd4 variation in subjects from the collected database, a comparison of the frequency of its occurrence in patients with various vitreoretinopathies and in full-term infants was made (healthy newborns used as controls). A disproportionate percentage of infants and children with a diagnosis of ROP or FEVR have this Fzd4 mutation compared to the general population. Furthermore, it was discovered that ROP patients with this Fzd4 sequence variation have lower birth weights than expected at their respective gestational ages. This suggested that Wnt signaling via the Fzd4 receptor is important for fetal (and possibly placental) growth and may be a predictor of premature birth. Based on these observations it was concluded that it may be beneficial to screen premature infants for this variation.

In a previous study of premature mono- and di-zygotic twins, (Bizzarro M J, Hussain N, Jonsson B, et al. Genetic susceptibility to retinopathy of prematurity. Pediatrics 2006; 118(5):1858-63), determined that there is a genetic predisposition for ROP. The similar phenotypes of ROP and FEVR prompted many investigators to look at Wnt-signaling associated with the Norrin-FZD4 pathway (and associated genes) as possible candidates for this genetic predisposition to develop ROP. Indeed, several studies have reported Fzd4, NDP and LRP5 mutations in ROP patients and these appear to be particularly associated with more severe ROP. The first mutations discovered were located in the 5' UTR of the NDP gene. More recently, a study reported finding 13% (7/53) advanced ROP patients had either Fzd4 (3) or LRP5 (4) mutations (Kondo 2013). Similarly, an additional study by Ells et al. (Ells A, Guernsey D L, Wallace K, et al. Severe retinopathy of prematurity associated with FZD4 mutations. Ophthalmic Genet 2010; 31(1):37-43) found three Fzd4 mutations (Arg466Trp, Ala370Gly & Lys203Asn) in a group of 71 severe ROP patients and no Fzd4 mutations in 33 patients with mild or no ROP. Both studies concluded that FZD4 mutations may have role in the development or exacerbation of ROP. Interestingly, in the same study Ells et al. found (P33S;P168S) or either mutation alone in 10% of their severe ROP patients and in only 3% of patients with mild to no ROP. However, since Ells et al. also found (P33S;P168) in 7% of subjects in a group of random Caucasian samples, Ells et al. could not make a conclusion regarding the causality of the variation.

The three Fzd4 mutations found in the Ells et al. study were not located in important functional areas of the protein. Since relatives with the mutations did not have FEVR, the investigators concluded that these are milder mutations that may exacerbate retinopathy in premature infants. A potential mechanism for these milder Fzd4 mutations was recently reported by Milhem et al. (Milhem R M, Ben-Salem S, Al-Gazali L, et al. Identification of the cellular mechanisms that modulate trafficking of frizzled family receptor 4 (FZD4) missense mutants associated with familial exudative vitreoretinopathy. Invest Ophthalmol Vis Sci 2014; 55(6): 3423-31) These investigators used confocal immunofluorescence microscopy to demonstrate localization of several Fzd4 mutants, including P33S, in the endoplasmic reticulum when expressed in HeLa cells, indicating defective trafficking of the protein to the plasma membrane. Milhem et al. purposed that this defective trafficking may lead to haploinsufficiency of the frizzled4 protein. P33S is located in the signal peptide region of the protein, three 278 residues before the cleavage site between residues 36 & 37. It is plausible that the P33S mutation interferes with the cleavage of the signal peptide and therefore traps Fzd4 in the endoplasmic reticulum. Although Milhem et al. did not test the P168S mutant, several other Fzd4 mutants (G36N, H69Y, M105T, C204R, C204Y, G488D) were shown to translate proteins with the same trafficking defect.

Haploinsufficiency might also explain the discrepancy in activities seen in Wnt reporter assays of cells transfected with Fzd4 mutants. Qin et al. (Qin M, Kondo H, Tahira T, et al. Moderate reduction of norrin signaling activity associated with the causative missense mutations identified in patients with familial exudative vitreoretinopathy. Hum Genet 2008; 122(6):615-23) showed a reduction of 33% and 44% for two missense Fzd4 mutants, M105V & R417Q, respectively, and a reduction of 99% for one nonsense mutation (W319X) when compared to wild type Fzd4. When the (P33S;P168S) mutant Fzd4 were expressed in HEK293 cells a 15% reduction in TCF/LEF (Wnt-canonical signaling) promoter driven luciferase activity was noted compared to the activity generated by wild type Fzd4. However, another mutant, C117R, that affects Fzd4 ligand binding region, more drastically decreased the luciferase reporter activity. Although the (P33S;P168S)-induced reduction in the Wnt reporter activity was small, it may be that under conditions where there is an increased demand for Norrin:Fzd4 signaling, it is relevant. However, caution should be taken not to over interpret the in vitro results since the conditions are very different from those in the retina and the complex disorders associated with the pathway In phase 1 of the aforementioned 1000 Genomes Project the (P33S;P168S) variation was found in 20 out of 1092 random subjects (1.8 301%). The rate of the (P33S;P168S) haplotype varied among ethnic groups; AFR (1.2%, 3/246), AMR (5%, 9/181), EUR (1.1%, 8/379) and ASN (0/286). Interestingly, Chi-squared analysis comparing the frequency of the mutation in subjects from the 1000 Genomes project to that found in ROP patients in this study (7.5%), revealed a significant difference between the two groups (p=4.6E-04). The significance was even higher when including the three ROP patients that had either P33S or P168S alone (p=1.8E-07). The frequency of the variation was also significantly higher in FEVR patients (5.5%) when compared to subjects in the 10000 Genomes project (p=2.4E-03). To the contrary, the rate in healthy newborns (3.1%) was not significantly different from that predicted based on the subjects in the 1000 Genomes project (p=1.7E-01). Perhaps some of the wide variation in the reported rates of the (P33S;P168S) haplotype in control subjects can be explained by undiagnosed FEVR.

A previous study conducted by Applicants examined the asymptomatic relatives of FEVR patients and found that many had clinical findings consistent with FEVR (58% with stage 1 or 2 and 21% with stage 3 or greater) and yet they had no functional deficits.

Thus, there exists a need for a method to screen if a woman is prone for a pre-term birth. There further exists a need clinical intervention to mitigate inclination towards pre-term birth.

SUMMARY OF THE INVENTION

A method for determining the necessity of a pre-term birth treatment is provided based on obtaining a biological sample from a subject. The biological sample is analyzed for the presence of (P33S;P168S) Frizzled4 (Fzd4) gene variation. The subject or a fetus thereof is then treated for a proclivity to pre-term birth. The Fzd4 protein itself can also be analyzed for the (P33S;P168S) Fzd4 mutation.

BRIEF DESCRIPTION OF THE DRAWINGS

These and other aspects of the present invention will be elucidated in the accompanying drawings and following detailed description of the invention.

DETAILED DESCRIPTION OF THE INVENTION

The present invention has utility as a method for predicting premature births by detecting either a specific genetic mutation in Fzd4 or the Fzd4 protein conformation in a female subject, either prior to or during pregnancy or a fetus she carries. It is appreciated that screening a father as a subject also is of value in providing genetic counseling and follow-up testing if the father of a fetus carries the Fzd4 (P33S; P168S) variation. The Fzd4 protein variations at amino acids 33 and 168 thereof from proline (P) to serine (S) are the basis for the present invention. The Fzd4 protein sequence (Accession: NP_036325) and nucleic acid sequence (GenBank assembly accession: GCA_000001405.26) are known.

Determining a genetic predisposition for pre-term birth allows for the treatment thereof during pregnancy, as well as avoiding unneeded treatments during in pregnancy of non-mutant female subjects and their fetuses. Embodiments of the present invention utilize the association between mutations affecting the Wnt-signaling receptor (Fzd4), inherited vitreoretinopathies and Retinopathy of Prematurity. Without intending to be bound to a particular theory, Wnt mutations, specifically including NDP or Fzd4, or downstream receptors in the pathway, create infertility, placental insufficiency and intra-uterine growth retardation, resulting in premature birth. The premature birth, and likely the underlying genetic alterations, lead to increased risk of ROP.

The following definitions are used herein with respect to the understanding of the present invention.

"Administering" is defined herein as a means of providing a composition to a subject. Such an administration can be by any route including, without limitation, oral, transdermal (e.g., oral mucosa), by injection (e.g., subcutaneous, intravenous, parenterally, intraperitoneally, intraocular), by inhalation (e.g., oral or nasal), or topical (e.g., eyedrops, cream, etc.). Pharmaceutical preparations are, of course, given by forms suitable for each administration route.

By "alteration" is meant a change (increase or decrease) in the expression levels or activity of a gene or polypeptide as detected by standard art known methods such as those described herein. As used herein, an alteration includes at least a 10% change in expression levels, preferably a 25% change, more preferably a 40% change, and most preferably a 50% or greater change in expression levels.

In this disclosure, "comprises," "comprising," "containing" and "having" and the like can have the meaning ascribed to them in U.S. Patent law and can mean "includes," "including," and the like; "consisting essentially of or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

By "control" is meant a standard or reference status.

"Detect" refers to identifying the presence, absence or amount of the analyte to be detected.

By "detectable label" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

As used herein, "obtaining" as in "obtaining an agent" includes synthesizing, purchasing, or otherwise acquiring the agent.

The term "patient" or "subject" refers to an animal which is the object of treatment, observation, or experiment. By way of example only, a subject includes, but is not limited to, a mammal, including, but not limited to, a human or a non-human mammal, such as a non-human primate, bovine, equine, canine, ovine, or feline.

"Pharmaceutically acceptable" refers to approved or approvable by a regulatory agency of the Federal or a state government or listed in the U.S. Pharmacopeia or other generally recognized pharmacopeia for use in animals, including humans.

"Pharmaceutically acceptable excipient, carrier or diluent" refers to an excipient, carrier or diluent that can be administered to a subject, together with an agent, and which does not destroy the pharmacological activity thereof and is nontoxic when administered in doses sufficient to deliver a therapeutic amount of the agent.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

By "reduces" is meant a negative alteration of at least 10%, 25%, 50%, 75%, or 100%.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/ PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

As used herein, the terms "treat," "treated," "treating," "treatment," and the like refer to reducing or ameliorating a disorder and/or symptoms associated therewith BRB compromise.

Unless specifically stated or obvious from context, as used herein, the term "or" is understood to be inclusive. Unless specifically stated or obvious from context, as used herein, the terms "a," "an," and "the" are understood to be singular or plural.

As used herein, "variation" and "mutation" are used synonymously with respect to Fzd4 (P33S; P168S) amino acid changes in Fzd4 and the coding nucleic acids.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

According to the present invention, the healthy newborns found to carry (P33S;P168S) sequence variation, may have avascular retina. Although none of the 3 newborns had a family history of eye disease, two of the mothers had histories of previous miscarriages. Interestingly, a few studies have shown that Norrin-Fzd4 signaling may affect angiogenesis in the female reproductive system. Hseih et al. (Hsieh M, Boerboom D, Shimada M, et al. 440 Mice null for Frizzled4 (Fzd4−/−) are infertile and exhibit impaired corpora lutea formation and function. Biol Reprod 2005; 73(6): 1135-46) found that markers for angiogenesis and vascular formation are reduced in the corporo lutea of Fzd4 null mice and these mice are infertile. Hayashi et al. localized Fzd4 mRNA to vessels and stroma surrounding the mouse embryo. Similarly, norrin has been localized to the uterine blood vessels and decidual cells of rats, and NDP knockout mice have defects in vascular development and decidualization in pregnancy that leads to embryonic loss. In humans, the expression of NDP has been established in the placenta and Fzd4 expression has been localized to placental villous mesenchymal cells.

Without intending to be limited to a particular theory and based on the findings presented herein, the (P33S;P168S) Fzd4 gene variation is associated with FEVR and ROP. The variant was particularly prevalent in ROP patients with a GA≥26 weeks. Interestingly, in patients with a GA≥26 weeks, low BW per GA has been reported to be a risk factor for severe ROP. Therefore, it may be beneficial to screen premature infants for the presence of the variant so that these patients may be monitored more carefully. Additionally, a correlation of the variant and low BW per GA, indicates that defective Fzd4 signaling may play a role in placental insufficiency and intrauterine growth restriction. Thus, a blood test to screen for the presence of (P33S;P168S) in women who have high risk pregnancies is recommended to determine whether steps to mitigate the chances of a premature birth should be taken.

A retrospective genetic analysis of the Fzd4 gene was performed (Sanger sequencing). Participants with a diagnosis of Familial Exudative Vitreoretinopathy (FEVR), Norrie Disease (ND), Coats Disease, bilateral Persistent Fetal Vasculature (BPFV), and Retinopathy of Prematurity (ROP) were reviewed for presence of a Fzd4 mutation. Data retrieval included status of retinopathy (including staging when possible), gestational age and birth weight (when available), and family and birth histories. The analysis showed that the sequence variation (P33S;P168S) was the most prevalent Fzd4 mutation, and is statistically significant for ROP and FEVR (p=4.6E-04; p=2.4E-03, respectively), compared to full-term newborns (p=1.7E-01). Additionally, infants expressing the sequence variation tended to have significantly lower birth weights for respective gestational age (p=0.04). This suggests that the Fzd4 (P33S;P168S) mutation may be a risk factor for retinopathy and restricted intrauterine growth, and that testing for FZD4 mutations is useful in patients with suspected FEVR and ROP. The relatively high prevalence of the (P33S;P168) mutation in ROP and intrauterine growth restriction suggested it may be a marker for increased risk of developing ROP and pre-term birth as well.

An exemplary method for detecting the presence or absence of a Fzd4 (P33S;P168S) mutant protein in a biological sample involves obtaining a biological sample from a subject, such as a human, contacting the biological sample with a compound or an agent capable of detecting of the marker being analyzed, illustratively including an antibody or aptamer, and analyzing binding of the compound or agent to the sample after washing. Those samples having specifically bound compound or agent express the marker being analyzed. Samples illustratively include blood, muscoal tissue swabs, amniotic fluid, or other sources of subject cells or Fzd4 proteins.

An inventive method can be used to detect Fzd4 (P33S; P168S) mutant protein in a biological sample in vitro, as well as in vivo. The quantity of Fzd4 (P33S;P168S) mutant protein in a sample is compared with appropriate controls such as a first sample known to express detectable levels of the Fzd4 (P33S;P168S) mutant protein being analyzed (positive control) and a second sample known to not express detectable levels of Fzd4 (P33S;P168S) mutant protein (a negative control). For example, in vitro techniques for detection of a marker illustratively include enzyme linked immunosorbent assays (ELISAs), radioimmuno assay, radioassay, western blot, Southern blot, northern blot, immunoprecipitation, immunofluorescence, mass spectrometry, RT-PCR, PCR, liquid chromatography, high performance liquid chromatography, enzyme activity assay, cellular assay, positron emission tomography, mass spectroscopy, combinations thereof, or other technique known in the art. Furthermore, in vivo techniques for detection of a marker include introducing a labeled agent that specifically binds the Fzd4 (P33S;P168S) mutant protein into a biological sample or test subject. For example, the agent can be labeled with a radioactive marker whose presence and location in a biological sample or test subject can be detected by standard imaging techniques. Optionally, the Fzd4 (P33S;P168S) mutant protein specifically binding agent is bound to a substrate. It is appreciated that a bound agent assay is readily formed with the agents bound with spatial overlap, with detection occurring through discernibly different detection for first biomarker and each of at least one additional neuroactive biomarkers. A color intensity based quantification of each of the spatially overlapping bound biomarkers is representative of such techniques.

Any suitable molecule that can specifically bind Fzd4 (P33S;P168S) mutant protein is an antibody capable of binding to the Fzd4 (P33S;P168S) mutant protein. Preferably, an antibody is conjugated with a detectable label. Such antibodies can be polyclonal or monoclonal. An intact antibody, a fragment thereof (e.g., Fab or F(ab')2), or an engineered variant thereof (e.g., sFv) can also be used. Such antibodies can be of any immunoglobulin class including IgG, IgM, IgE, IgA, IgD and any subclass thereof. Antibodies for numerous inventive biomarkers are available from vendors known to one of skill in the art. The anti-Fzd4 (P33S;P168S) mutant protein antibody is optionally labeled. A person of ordinary skill in the art recognizes numerous labels operable herein. Labels and labeling kits are commercially available optionally from Invitrogen Corp, Carlsbad, Calif. Labels illustratively include, fluorescent labels, biotin, peroxidase, radionucleotides, or other label known in the art. Alternatively, a detection species of another antibody or other compound known to the art is used as form detection of a biomarker bound by an antibody.

Antibody-based assays are preferred for analyzing a biological sample for the presence of Fzd4 (P33S;P168S) mutant protein. Suitable western blotting methods are described are conventional, as well as immunosorbent assays (e.g., ELISA and RIA) and immunoprecipitation assays may be used. As one example, the biological sample or a portion thereof is immobilized on a substrate, such as a membrane made of nitrocellulose or PVDF; or a rigid substrate made of polystyrene or other plastic polymer such as a microtiter plate, and the substrate is contacted with an antibody that specifically binds Fzd4 (P33S;P168S) mutant protein. After washing, the presence of the antibody on the substrate indicates that the sample contained the marker being assessed. If the antibody is directly conjugated with a detectable label, such as an enzyme, fluorophore, or radioisotope, the presence of the label is optionally detected by examining the substrate for the detectable label. Alternatively, a detectably labeled secondary antibody that binds the marker-specific antibody is added to the substrate. The presence of detectable label on the substrate after washing indicates that the sample contained the marker.

Numerous permutations of these basic immunoassays are also operative in the invention. These include the biomarker-specific antibody, as opposed to the sample being immobilized on a substrate, and the substrate is contacted with Fzd4 (P33S;P168S) mutant protein conjugated with a detectable label under conditions that cause binding of antibody to the labeled marker. The substrate is then contacted with a sample under conditions that allow binding of the marker being analyzed to the antibody. A reduction in the amount of detectable label on the substrate after washing indicates that the sample contained the marker.

Although antibodies are preferred for use in the invention because of their extensive characterization, any other suitable agent (e.g., a peptide, an aptamer, or a small organic molecule) that specifically binds Fzd4 (P33S;P168S) mutant protein is optionally used in place of the antibody in the above described immunoassays. Methods for making aptamers with a particular binding specificity are known as detailed in U.S. Pat. Nos. 5,475,096; 5,670,637; 5,696,249; 5,270,163; 5,707,796; 5,595,877; 5,660,985; 5,567,588; 5,683,867; 5,637,459; and 6,011,020.

A myriad of detectable labels that are operative in a diagnostic assay for biomarker expression are known in the art. Agents used in methods for detecting Fzd4 (P33S; P168S) mutant protein are conjugated to a detectable label, e.g., an enzyme such as horseradish peroxidase. Agents labeled with horseradish peroxidase can be detected by adding an appropriate substrate that produces a color change in the presence of horseradish peroxidase. Several other detectable labels that may be used are known. Common examples of these include alkaline phosphatase, horseradish peroxidase, fluorescent compounds, luminescent compounds, colloidal gold, magnetic particles, biotin, radioisotopes, and other enzymes. It is appreciated that a primary/secondary antibody system is optionally used to detect one or more biomarkers. A primary antibody that specifically recognizes one or more biomarkers is exposed to a biological sample that may contain the biomarker of interest. A secondary antibody with an appropriate label that recognizes the species or isotype of the primary antibody is then contacted with the sample such that specific detection of the one or more biomarkers in the sample is achieved.

The present invention employs a step of correlating the presence or amount of Fzd4 (P33S;P168S) mutant protein in a biological sample with the severity of inclination towards pre-mature birth. Fzd4 (P33S;P168S) mutant protein measurement alone is shown herein to be highly effective in detecting a proclivity towards non-pathogenic pre-mature birth. The results of an inventive method to measure Fzd4 (P33S;P168S) mutant protein can help a physician or veterinarian determine the steps needed to preclude non-pathogenic premature birth for which there are currently indicators thereby reducing neonatal morbidity and neonatal intensive care treatment requirements.

The practice of an inventive method provides a test which can help a physician determine suitable therapeutics to administer for optimal benefit of the subject. One such treatment being administration of norrin protein or a synthetic truncate thereof that retains the therapeutic effect thereof.

An assay for detecting a non-pathogenic proclivity toward premature birth in a subject or a cell culture isolated therefrom is also provided. The assay includes: (a) a substrate for holding a sample isolated from a subject, the sample containing cells that can be assayed for (P33S;P168S) Fzd4 gene mutations or in the corresponding protein; (b) a Fzd4 (P33S;P168S) mutant protein specific binding agent; and (d) printed instructions for performing the assay illustratively for reacting: the specific binding agent with the biological sample or a portion of the biological sample to detect the presence or amount of Fzd4 (P33S;P168S) mutant protein. The inventive assay can be used to detect a proclivity toward premature birth for financial remuneration.

The assay optionally includes a detectable label such as one conjugated to the agent, or one conjugated to a substance that specifically binds to the agent, such as a secondary antibody.

The present invention is further detailed with respect to the following examples. These examples are not intended to limit the scope of the appended claims.

Example 1—Method of Experiment

Patients and controls (healthy newborns) were recruited to a study through a protocol approved by the internal review board and consented to participation. Diagnoses were made based upon fundus examination, family history, gestational age and wide field fluorescein angiography (when available) and the patients were categorized into 5 groups; FEVR, Possible FEVR (PFEVR), Norrie Disease (ND)/Bilateral PFV (BPFV), ROP and Coats Disease. Birth weights and gestational ages were obtained from the records of 56 and 60 ROP patient respectively.

A diagnosis of PFEVR was assigned to patients for whom a differential diagnosis (FEVR, PFVS, ND, ROP) could not be made upon clinical examination alone. Patients who had a peripheral avascular area but no other retinal vascular anomalies where also categorized as PFEVR. Norrie Disease and BPFV patients were categorized in the same group (ND/BPFV) since their phenotypes are similar and it is therefore difficult to distinguish between these two disorders clinically.

Genomic DNA was isolated from the leukocytes of patients diagnosed with FEVR (n=181), PFEVR (n=78), ROP (n=93), ND/BPFVS (n=61) and Coats Disease (n=8) using a Purgene Genomic DNA Purification Kit (Qiagen, Valencia, Calif.). For controls, a drop of blood was collected from healthy full-term newborns (n=98) and blotted onto FTA cards (GE Healthcare, Pittsburgh, Pa.). Genomic DNA-wasthen amplified from the cards using a GenomiPhi whole genome amplification kit (GE-Healthcare, Pittsburgh, Pa.) according to the kit instructions. Briefly, 3 mm punches were taken from the dried blood on FTA cards and transferred to reaction tubes. After washing, the disks were incubated over night with GenomiPhi Reaction mix containing Phi29 polymerase.

Example 2—Sequencing

The coding sequence (CDS) and flanking splice sites of the Fzd4 gene were amplified from Genomic DNA using Herculase II Fusion Enzyme (Agilent Technologies, LaJolla, Calif.). Four sets of primers were used for PCR amplification of the Fzd4 gene; one spanning exon 1 (285 bases) and three spanning overlapping sections of exon 2 (1326 bases). The touchdown amplification conditions were as follows; 1 cycle at 98° C. for 3 min followed by 12 cycles of [30 sec at 98° C., 30 sec at 66° C. (−1° C./cycle), 35 sec at 72° C.] and then 25 cycles of [30 sec at 98° C. 30 sec at 55° C., 35 sec at 72° C.} and a final extension cycle for 1 min at 72° C. The amplified DNA was then cleaned of excess primer and unincorporated nucleotides using a QIAquickMultiwell Purification Kit (Qiagen, Valencia, Calif.) and aliquots were removed 118 and used for dye terminating cycle sequencing reactions using Beckman Dye Terminator Cycle Sequence Quick Start Kit (Beckman Coulter, Inc., Fullerton, Calif.). A Beckman CEQ8000 DNA Autosequencer was then used to determine DNA sequences.

TCF/LEF (Wnt-canonical) Pathway Activity Assay

HEK293 cells (ATCC, Manassas, Va.) were seeded into 24 well plates and transfected using Lipofectamine2000 (Life Technologies, Grand Island, N.Y.) after reaching 80-90% confluence. DNA mixes were made consisting of 100 ng each of TCF/LEF reporter mix (Cignal Reporter Kit, SABiosciences, Valencia, Calif.), LRP5 and Fzd4 or Fzd4 mutant constructs. LRP5, Fzd4 and two custom Fzd4 mutant clones, (P33S;P168S) and C117R, were purchased from Origene (Rockville, Md.). Transfections were carried out for 5 hours in OptiMEM media containing no antibiotics or serum. Twenty four hours after transfection, the media was replaced with DMEM media (10% FBS) containing 200 ng/ml of human recombinant norrin (R&D Systems, Minneapolis, Minn.). At the end of a 24 hour norrin treatment, the cells were lysed and Firefly and Renilla Luciferase activity was measured using a Dual-Luciferase Reporter assay kit (Promega, Madison, Wis.) and a Turner Biosystems Luminometer (Promega, Madison, Wis.). Four experiments were run in triplicate for each Fzd4 type.

Example 3—Statistical Analysis

Pearson's Chi-squared analysis was used to compare the frequency of the Fzd4 gene 140 variation in different cohorts. The Canadian gender-specific reference, based upon live and still births, was used to obtain normal mean birth weights. Male and Female weights were averaged to generate a mean for each age. Small for gestational age (SGA) was defined as being below the 10th percentile. Student's t-test analysis was used to determine significance of differences in birth weight deviations from normal.

Example 4—Prevalence of Fzd4 Mutations

Eighteen Fzd4 variations were found in 50 patients (42probands). Two nonsense mutations, one deletion/insertion and 14 missense mutations were located in the CDS. Notably, of 42 probands with Fzd4 mutations, 20 had the same compound sequence variation (P33S;P168S) and four had one of the variations alone (1 with P33S and 3 with P168S) as shown in Table 1. The compound sequence variation (alone or in combination) was present in 5.4% (28/520) of the subjects enrolled in the study, ranging from 3% of healthy full-term newborns to 10.7% of infants with ROP as shown in Table 2.

In addition, one ROP patient had the P33S variation alone and 3 patients (2 ROP and 1 FEVR) had only the P168S variation.

Other (non-(P33S;P168S) mutations affecting Fzd4 were found in the DNA sequence of patients with FEVR (n=11) and ROP (n=1) (Table 1). Additionally, one ROP patient with the P33S variation also carried a missense variation in the 3'UTR of the NDP gene (c.417 G>A).

Furthermore, since the (P33S;P168S) variation has been reported in random samples, 98 full-term newborns were also screened for the presence of the compound variation (or either mutation alone). The variation was discovered in 3.1% of the newborns (3/98). Although none of the three had a family history of eye disease, the mothers of two newborns had a history of miscarriage. Chi-squared analysis demonstrated that the difference in frequency of (P33S;P168S) in full term newborns and ROP patients, in this database, was close to being statistically significant (p=0.06). This

TABLE 1

Mutations in Fzd4 gene

| Location | Protein Change | Base Change | no. of Patients w/mutation | no. of Probands w/mutation | Diagnosis |
| --- | --- | --- | --- | --- | --- |
| Exon 1 (CDS) | | Del/inser c.40 | 1 | 1 | F |
| | | c.242 ins G | 1 | 1 | PFVS |
| | S51T | c.151 T > A | 1 | 1 | F |
| | G57C | c.169 G > T | 2 | 1 | F |
| | H69Y | c.205 C > T | 1 | 1 | possF |
| Exon 2 (CDS) | C117R | c.349 T > C | 2 | 2 | F |
| | C181Y | c.542 G > A | 4 | 2 | F |
| | E217G | c.650 A > G | 1 | 1 | PFVS |
| | R253H (homo) | c.758 G > A | 1 | 1 | F |
| | E278E | c.834 A > G | 2 | 2 | PFVS |
| | W335X | c.1004 G > A | 1 | 1 | possF |
| | K358N | c.1074 A > C | 2 | 1 | F |
| | G424E | c.1271 G > A | 1 | 1 | ROP |
| | Q505X | c.1513 C > T | 1 | 1 | F |
| | G530E | c.1589 G > A | 1 | 1 | F |
| Exon 1 & Exon 2 | P33S; P168S | c.97 C > T; c.502 C > T | 24 | 20 | F, ROP, possF, ND, FT |
| | P33S | c.97 C > T | 1 | 1 | ROP |
| | P168S | c.502 C > T | 3 | 3 | FEVR & ROP |

ND: Norrie Disease,
F: Familial Exudative Vitreoretinopathy,
PFVS: Persistent Fetal Vasculature Syndrome,
ROP: retinopathy of prematurity,
PossF: possible FEVR

TABLE 2

(P33S, P168S) and type of disease

| Disorder | No. of Patients | %/(#) with (P33S; P168S) | %/(#) with (P33S; P168S) or either alone | No. with P33S alone | No. with P168S alone |
| --- | --- | --- | --- | --- | --- |
| FEVR | 181 | 5.5% (10) | 6.1% (11) | 0 | 1 |
| PFEVR | 78 | 3.8% (3) | 3.8% (3) | 0 | 0 |
| Norrie or BPFV | 61 | 1.6% (1) | 1.6% (1) | 0 | 0 |
| ROP | 93 | 7.5% (7) | 10.7% (10) | 1 | 2 |
| Coat | 8 | (none) | (none) | 0 | 0 |
| Healthy Newborns | 98 | 3.1% (3) | 3.1% (3) | 0 | 0 |

Participants were classified by the diagnosis made at the time of presentation. The majority of patients with the (P33S;P168S) variation had a diagnosis of FEVR or ROP (FEVR, n=10; ROP,n=7) with a few patients carrying the diagnosis of PFEVR (n=3), and ND/BPFVS (n=1) (Table 2).

prompted further exploration for the presence of (P33S; P168S) in the general population using data from the 1000 (Genomes Project 1000 Genomes Project Consortium, Abecasis G R, Auton A, et al. An integrated map of genetic variation from 1,092 human genomes. Nature 2012; 491 (7422):56-65), a large international research database cataloguing genetic variations in a heterogeneous population. This evaluation revealed a significant difference between the (healthy) subjects of the 1000 Genomes Project and both the ROP (p=4.6E-04) and FEVR (p=2.4E-03) patients in the study described herein, but not the full-term infants (p=1.7E-01). This suggested that the Fzd4 compound sequence variation (P33S;P168S) strongly correlates with vitreoretinal changes associated with FEVR and ROP.

Example 5—Intrauterine Growth Restriction

Figure 1:
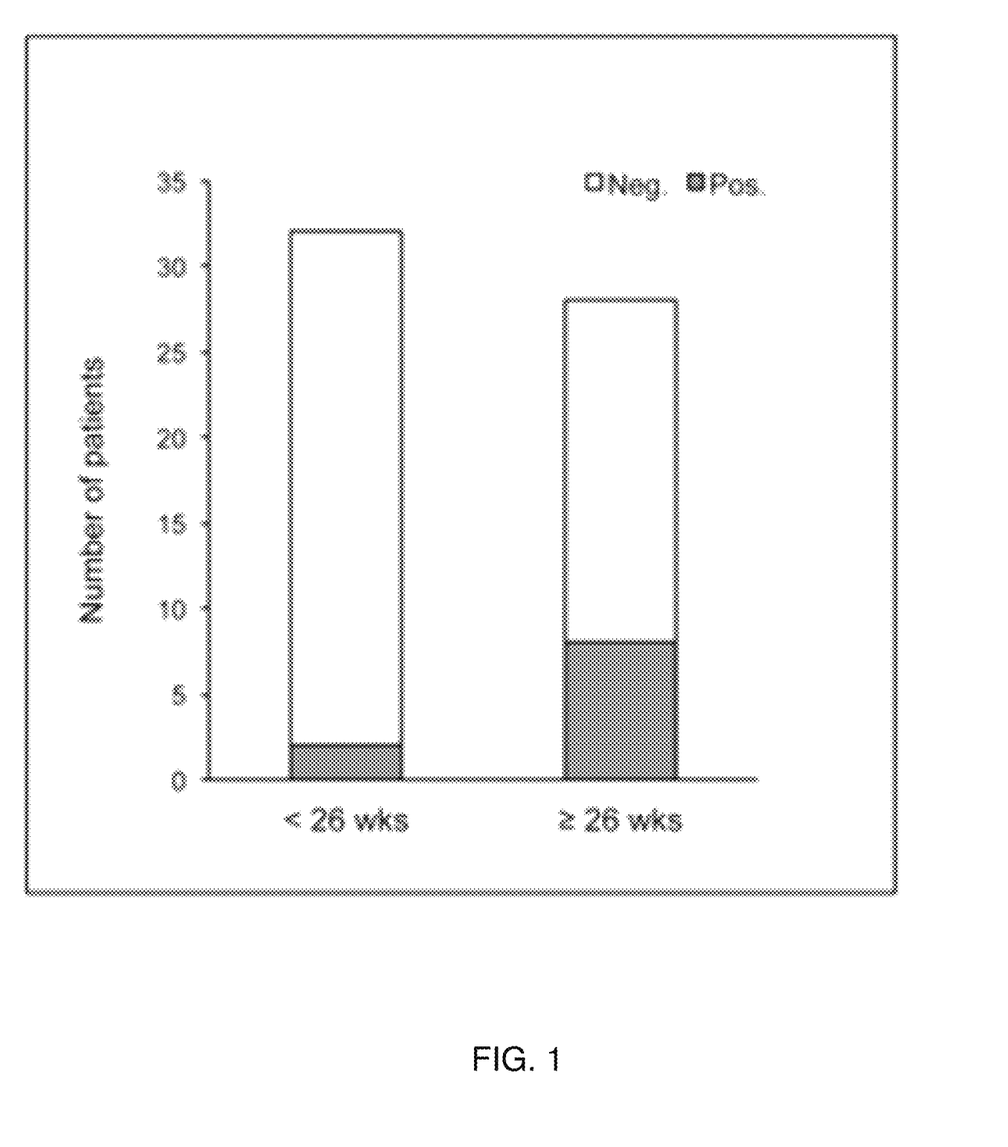
FIG. 1 is a graphical illustration of the prevalence of the Fzd4 (P33S; P168S) variation distributed by gestational age.

Birth weight (BW) and gestational age (GA) were also evaluated in newborns and ROP patients, as these are known to be risk factors for the development of retinopathy. Full term newborns had an average BW of 186 grams and an average GA of 39 weeks. For ROP patients, GA ranged from 23 weeks to 32 weeks with an average of 26 weeks. Since we noted that the majority of the ROP patients with the (P33S;P168S) variation had a GA above 26 weeks, we looked at the frequency of (P33S;P168S or either alone) in two groups; those with a GA below 26 weeks (ultra-premature infants) and those with a GA at or above 26 weeks as shown in FIG. 1. This distinction was chosen as the risk for developing retinopathy is higher in ultra-premature infants. Two of the 32 (6%) ROP patients with a GA below 26 weeks were positive for (P33S;P168S), whereas eight of the 28 (29%) patients with a GA at or above 26 weeks, were positive for (P33S;P168S)

Figure 2:
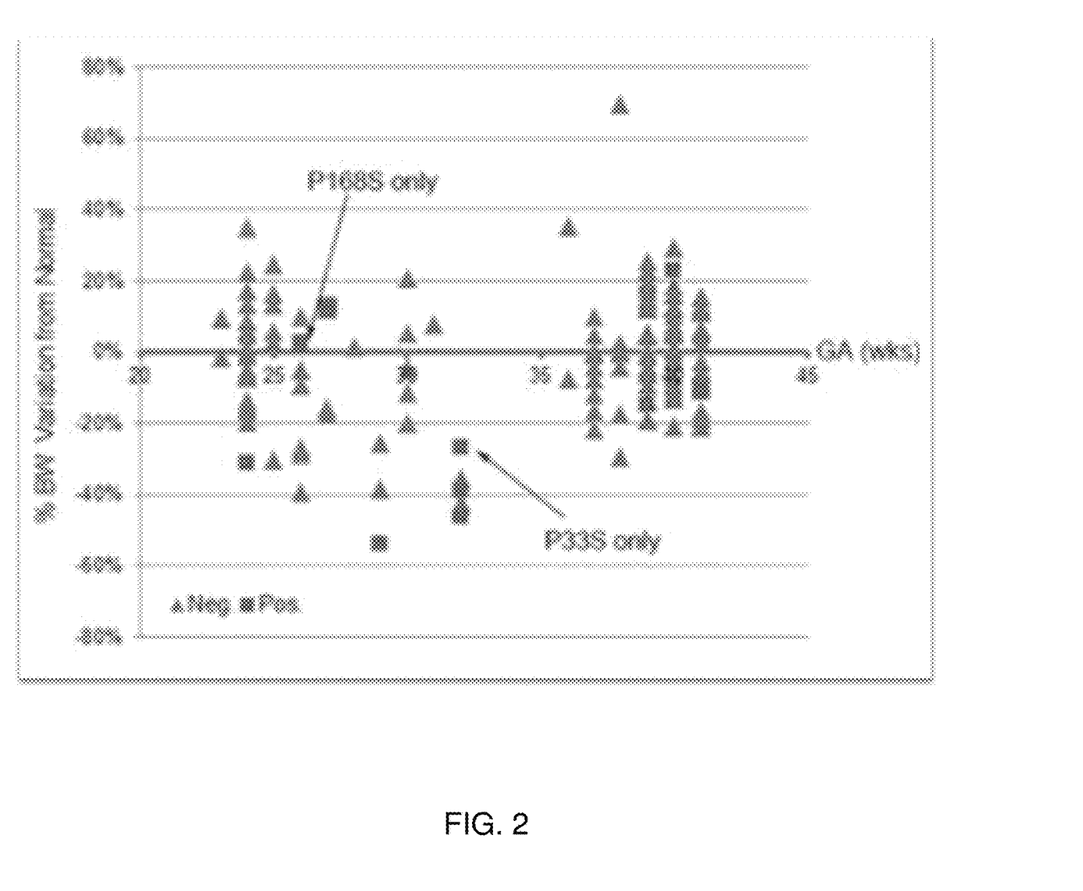
FIG. 2 is a scatter plot of birth weight versus gestational age.
Figure 3:
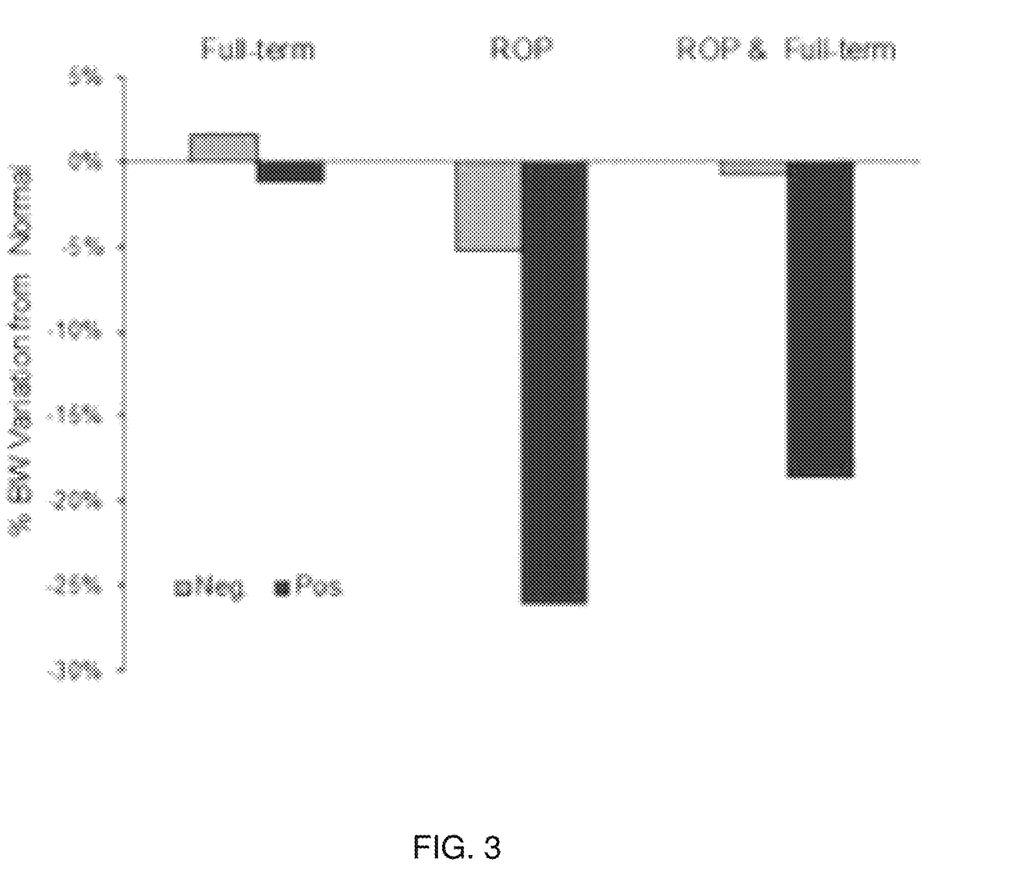
FIG. 3 is a graph depicting birth weight variation based on the presence or absence of the Fzd4 (P33S; P168S) variation.

Although the majority of ROP patients with the (P33S; P168S) variation had a GA above 26 weeks, it is noted many with lower than expected birth weights for gestational age as shown in FIG. 2. For this reason, a comparison was made of the differences in the birth weights of the ROP patients to that of expected birth weights at their corresponding gestational ages based on the Canadian gender-specific reference (Kramer M S, Platt R W, Wen S W, et al. A new and improved population-based Canadian reference for birth weight for gestational age. Pediatrics 2001; 108(2):E35). FIG. 3 shows the percentage of variation from expected birth weights of the ROP patients and full-term infants in the database. The distribution of the "% BW variation from normal" relative to GA for individual subjects can be seen in FIG. 2. On average, ROP infants with the (P33S;P168S) variation weighed 26% less than expected for GA (range from −54% to +13%) (see FIG. 2 and FIG. 3). This is in contrast to infants with ROP without the compound sequence variation, who averaged only 5% below expected weight (range from −42% to +35%). Interestingly, one of the ROP patients with the variation and a BW 3% above the normal, had only the (P168S) variant. The percentage below the mean was significantly larger in ROP patients that carried the compound variation compared to those who did not (p=0.04) (FIG. 3). Conversely, full term infants, on average, had birth weights that were 2% above expected weight (range −29 to +70%) (see FIG. 2 and FIG. 3). The three full term infants with the (P33S;P168S) variation had −15%, −11% and +23% percentage variations from mean expected birth weights (see FIG. 2).

Furthermore, the number of subjects that were small for gestational age (below 10th percentile in Canadian growth charts) were also examined. It was found that 12 out of 56 (21.4%) ROP patients were SGA including 5 of 7 (71.4%) carrying the compound variation (P33S;P168S). Altogether, this suggests that lack of fetal growth may be associated with pre-term birth and that a genetic predisposition may be causative for intrauterine growth retardation.

Three healthy newborns were found to carry (P33S; P168S) sequence variation, yet may have avascular retina. Although none of the 3 newborns had a family history of eye disease, two of the mothers had histories of previous miscarriages. Interestingly, a few studies have shown that Norrin-Fzd4 signaling may affect angiogenesis in the female reproductive system. Hseih et al. (Hsieh M, Boerboom D, Shimada M, et al. 440 Mice null for Frizzled4 (Fzd4−/−) are infertile and exhibit impaired corpora lutea formation and function. Biol Reprod 2005; 73(6):1135-46) found that markers for angiogenesis and vascular formation are reduced in the corpora lutea of Fzd4 null mice and these mice are infertile. Hayashi et al. localized Fzd4 mRNA to vessels and stroma surrounding the mouse embryo.

Example 6—Wnt Canonical Activity

Figure 4:
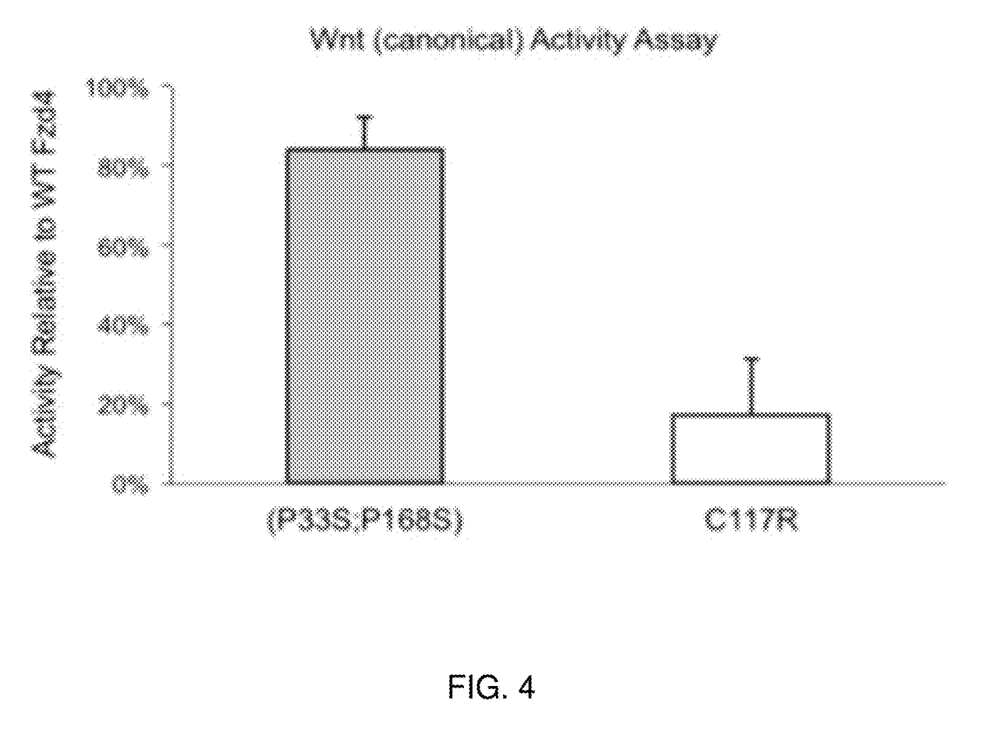
FIG. 4 is a graph of canonical pathway activation of the Fzd4 (P33S; P168S) variation.

Based on the high prevalence of the sequence variation (P33S;P168S) in patients with FEVR and ROP, the effect of this mutation on Wnt-pathway activity was also investigated. Previous investigations have shown a wide variability in Wnt-signaling activation with various mutations affecting the receptor (Fzd4). It has been suggested that the severity of retinopathy may correlate with the degree of dysfunctional pathway activation and that genetic testing may be helpful in patient management. To assess the ability of the (P33S;P168S) variant to activate signaling downstream of Fzd4, Wnt activated luciferase reporter assays were performed. Mutant (P33S;P168S) Fzd4 reduced Wnt reporter activity by 15% compared to wild type Fzd4 activity as shown in FIG. 4. Another Fzd4 mutant occurring in the database, C117R, reduced the activity much further. C117R reduced Wnt activity by 74% compared to that of the wild type Fzd4. Of note, both patients carrying the C117R mutation had severe exudation with retinal detachment, consistent with the depression of claudin 5 and subsequent breakdown of the endothelial tight junctions that occurs when the Fzd4 receptor is blocked. This suggests a mild dysfunction in receptor activation with the (P33S;P168S) variation and may explain its high prevalence in the population.

The (P33S;P168S) variation was detected more often than any other Fzd4 mutation in this cohort and was the only mutation found in a cohort of healthy full-term infants. Patients with a diagnosis of ROP had the highest frequency of the (P33S;P168S) variation (7.5%) (see Table 2). The occurrence of the variation was lower in the other cohorts; FEVR (5.5%), PFEVR (3.8%), ND/BPFVS (1.6%). When including subjects with either P33S or P168S variation alone the prevalence increased to 10.7% of ROP patients and 6.1% of FEVR patients.

REFERENCES CITED van der Horst P H, Wang Y, van der Zee M, Burger C W, Blok L J. Interaction between sexhormones and WNT/β-catenin signal transduction in endometrial physiology and disease. Mol Cell Endocrinol. 2011 Jun. 22.

Sonderegger S, Pollheimer J, Knöfler M. Wnt signalling in implantation, decidualisation and placental differentiation—review. Placenta. 2010 October; 31(10):839-47.

Matsuura K, Jigami T, Taniue K, Morishita Y, Adachi S, Senda T, Nonaka A, Aburatani H, Nakamura T, Akiyama T. Identification of a link between Wnt/β-catenin signalling and the cell fusion pathway. Nat Commun. 2011 Nov. 22; 2:548. doi: 10.1038/ncomms1551.

Kaloglu C, Cesur I, Bulut H E. Norrin immunolocalization and its possible functions in rat endometrium during the estrus cycle and early pregnancy. Dev Growth Differ. 2011 September; 53(7):887-96. doi: 10.1111/j.1440-169X.2011.01295.x. Epub 2011 Sep. 7.

Macdonald L J, Sales K J, Grant V, Brown P, Jabbour H N, Catalano R D. Prokineticin 1 induces Dickkopf 1 expression and regulates cell proliferation and decidualization in the human endometrium. Mol Hum Reprod. 2011 October; 17(10):626-36. doi: 10.1093/molehr/gar031. Epub 2011 May 5.

References cited herein are incorporated by reference to the same extent as if each reference was individually and explicitly incorporated by reference.

As a person skilled in the art will recognize from the previous detailed description and from the figures and claims, modifications and changes can be made to the preferred embodiments of the invention without departing from the scope of this invention defined in the following claims.

The invention claimed is:

1. A method for determining the necessity of a pre-term birth treatment comprising:
  obtaining a biological sample of at least one source of subject cells or Frizzled4 (Fzd4) proteins from a pregnant subject;
  analyzing the biological sample for the presence of (P33S; P168S) Fzd4 gene variation;
  detecting the presence of (P33S;P168S) Fzd4 gene variation in the biological sample, thereby indicating the necessity of a pre-term birth treatment; and
  treating the pregnant subject identified as having the (P33S;P168S) Fzd4 gene variation for at least one of: intrauterine growth restriction, placental insufficiency, or risk of giving birth prematurely, thereby reducing the risk for at least one of the following fetal risks due to pre-term birth: Retinopathy of Prematurity (ROP), Familial Exudative Vitreoretinopathy (FEVR), or low birthweight per gestational age.

2. The method of claim 1, wherein said subject is a mammal.

3. The method of claim 1 wherein the subject is a human.

4. The method of claim 1 where the biological sample is a blood sample.

5. The method of claim 1 where the biological sample comprises leukocytes.

6. The method of claim 1 where the biological sample is amniotic fluid.

7. The method of claim 1 where the biological sample is a mucosal tissue swab.

* * * * *